US004001662B2

United States Statutory Invention Registration [19]

[11] Reg. Number: H1662

Nishimura et al.

[45] Published: Jul. 1, 1997

[54] CHEMICALLY MODIFIED LYMPHOKINE AND PRODUCTION THEREOF

[76] Inventors: Osamu Nishimura, 123-502, 2 Higashitoyonakacho 5-chome, Toyonaka, Osaka, Japan, 560; Masahiko Fujino, 10-7, Hibarigaoka 2-chome, Takarazuka, Hyogo, Japan, 665

[21] Appl. No.: 519,280

[22] Filed: Apr. 5, 1990

Related U.S. Application Data

[60] Continuation of Ser. No. 407,419, Sep. 14, 1989, which is a division of Ser. No. 919,544, Oct. 14, 1986, which is a continuation of Ser. No. 707,063, Mar. 15, 1985, abandoned.

[30] Foreign Application Priority Data

Mar. 6, 1984 [WO] WIPO ..... PCT/JP84/00085
Dec. 5, 1984 [WO] WIPO ..... PCT/JP84/00575

[51] Int. Cl.[6] ..... A61K 38/20; A61K 38/21; C07K 14/55; C07K 14/555

[52] U.S. Cl. ..... 252/182.12; 514/12; 530/351; 530/402; 530/410; 424/85.1; 424/85.2; 252/182.23

*Primary Examiner*—Richard D. Lovering
*Assistant Examiner*—John M. Covert

[57] ABSTRACT

The invention provides chemically modified lymphokines comprising a lymphokine moiety and at least one polyethylene glycol moiety of the formula: $R\text{-}(O\text{—}CH_2CH_2)_n$ wherein R is a protective group for the terminal oxygen and n is at least one, bonded directly to at least one primary amino group of the lymphokine moiety, and a method of producing the same.

The chemically modified lymphokines according to the invention can be produced by reacting a lymphokine with an aldehyde of the formula $R\text{-}(O\text{—}CH_2CH_2)_{n-1}O\text{—}CH_2CHO$ wherein R and n are as defined above, in the presence of a reducing agent.

The chemically modified lymphokines according to the invention are useful as drugs, among others.

1 Claim, 4 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

CHEMICALLY MODIFIED LYMPHOKINE AND PRODUCTION THEREOF

This is a continuation of application Ser. No. 07/407,419 filed on Sep. 14, 1989, pending, which is a divisional of application Ser. No. 06/919,544, filed on Oct. 14, 1986, pending, which is a file wrapper continuation application of application Ser. No. 06/707,063, filed Mar. 15, 1985 now abandoned.

Lymphokines such as interferons (hereinafter sometimes abbreviated as IFNs) and interleukin-2 (hereinafter sometimes abbreviated as IL-2) are considered to be of clinical value for the treatment of viral infections and malignancies and recent technological advances in genetic engineering have made it in principle possible to produce such lymphokines on large scales. It is known that the clearance of lymphokines administered to the living body is in general very short. In the case of lymphokines derived from heterologous animals, it is anticipated that antibodies may be produced in some instances and cause severe reaction such as anaphylaxis. Therefore, technology development is desired which leads to delayed clearance of lymphokines used as drugs, with their activity retained, and further to decrease in their antigenicity. To achieve this object, chemical modification of lymphokines is a very effective means. Such chemical modification is expected to result in delayed clearance in the living body, decreased antigenicity and, further, increased physiological activity. From the practical viewpoint, the significance of chemical modification of lymphokines is thus very great.

Generally, in chemically modified physiologically active proteins, a method is required by which said proteins can be chemically modified while retaining their physiological activity. Polyethylene glycol methyl ether is considered to have no antigenicity and therefore is used in chemical modification of proteins. The introduction of said substance into proteins is generally performed by way of the intermediary of cyanuric chloride. However, cyanuric chloride is toxic per se and the possible toxicity of its degradation products in vivo remains open to question. Therefore, cyanuric chloride should be used with caution. Furthermore, the reaction involved requires a pH on the alkaline side and therefore the above-mentioned method of modification has a drawback in that it cannot be applied to proteins liable to inactivation under alkaline conditions.

U.S. Pat. No. 4,002,531 discloses a method of producing monoalkylpolyethylene glycol derivatives of enzymes. However, the method disclosed therein, which uses sodium borohydride at pH 8.5, when applied to lymphokines, may possibly destroy the physiological activity of lymphokines and therefore may not serve as an effective method of production. Furthermore, said patent specification does not provide any suggestion as to a means for delaying the in vivo clearance of the enzyme derivatives and such a means in otherwise unknown in the prior art.

There is also known a method of introducing a low molecular aldehyde such as formaldehyde, acetaldehyde, benzaldehyde or pyridoxal into physiologically active proteins in the presence of a boron-containing reducing agent [Methods in Enzymology, 47, 469 478 (1977); Japanese Patent Unexamined Publication No. 154 596/83]. However, application of said method to lymphokines fails to achieve effective delay in clearance. Rather than a decrease in antigenicity, it is possible that the low molecular aldehyde introduced may serve as a hapten to thereby provide said lymphokines with immunogenicity.

The present invention overcomes the above difficulties.

This is invention provides chemically modified lymphokines comprising a lymphokine moiety and at least one polyethylene glycol moiety of the formula $R-(O-CH_2-CH_2)_n$ (I) wherein R is a protective group for the terminal oxygen atom and n is at least one, bonded directly to at least one primary amino group of the lymphokine moiety and a method of producing the same.

In the present specification, the term "lymphokine" includes soluble factors released from lymphocytes and involved in cellular immunity and substances equivalent thereto in physiological activity.

Thus, the lymphokines may be genetically engineered products, products derived from various animals including humans and further include substances similar in structure and in physiological activity thereto.

For instance, there may be mentioned various interferons [interferon-α (IFN-α), interferon-β (IFN-β), interferon-γ (IFN-γ)], IL 2, macrophage differentiating factor (MDF), macrophage activating factor (MAF), tissue plasminogen activator, and substances similar in structure and in physiological activity thereto.

Examples of said substances similar in structure and in physiological activity are substances having the structure of IFN-γ except for the lack of 2 to 4 amino acids at the N-terminal thereof (U.S. pat. appl. Ser. No. 685,819 claiming the priority PCT/JP84/00292), various IFN-γ fragments lacking in the C terminal portion of IFN-γ (e.g. 15K species; U.S. pat. appln. Ser. No. 534,038), substances having the structure of IL-2 except for the lack of the N-terminal amino acid thereof (EPC (laid open) 91539) or the lack of 4 amino acids from the N-terminal portion (Japanese Patent Application 58-235638 filed Dec. 13, 1983) and substances having the structure of IL-2 except for the lack of one or more constituent amino acids with or without one or more substitute amino acids in place of said missing one or ones, for example the IL-2 analog containing serine in lieu of the 125th amino acid cysteine (EPC (laid open) 104798).

Preferred among such lymphokines are IFN-α, IFN-γ [consisting of 146 amino acids (EPC (laid open) 0089676)], IFN-γ lacking in two N-terminal amino acids (IFN-γ d2), IFN-γ lacing in three N-terminal amino acids (IFN-γ d3), and IL-2.

The lymphokines to be used in the practice of the invention preferably have a molecular weight of 5,000 to 50,000, more preferably 10,000 to 30,000.

The primary amino group of lymphokines includes the N-terminal α-amino group and the ε-amino group of the lysine residue.

Referring to the group represented by the above formula (I), the terminal oxygen-protecting group R is, for example, an alkyl or alkanoyl group. The alkyl group is preferably an alkyl of 1 to 18 carbon atoms, more preferably a lower ($C_{1-4}$) alkyl, such as methyl, ethyl, propyl, i-propyl, butyl, i-butyl, sec-butyl or t-butyl. The alkanoyl group is preferably an alkanoyl of 1 to 8 carbon atoms, more preferably a lower ($C_{1-6}$) alkanoyl, such as formyl, acetyl, propionyl, butyryl, i-butyryl or caproyl. The positive integer n is preferably not more than 500, more preferably 7 to 120.

The group of formula (I) preferably has a molecular weight of not more than 25,000, more preferably 350 to 6,000. From the viewpoints of physiological activity retention and clearance delaying effect, the group of formula (I) preferably has a molecular weight corresponding to 1 to 10%, more preferably 2 to 5% of the molecular weight of the lymphokine to be modified.

The chemically modified lymphokine according to the invention consists of a lymphokine moiety and the group of formula (I) directly bonded to at least one of the primary amino group of the lymphokine moiety.

When the N-terminal α-amino group is the only primary amino group in the lymphokine to be modified, the modified lymphokine has the group of formula (I) directly bonded to said amino group. When the lymphokine to be modified has one or more lysine residues in its molecule, the modified lymphokine has the group of formula (I) directly bonded to some percentage, preferably 15 to 80% (on the average), of said ε-amino groups. In this case, the N-terminal α-amino group may have or may not have the group of formula (I) directly bonded thereto.

The chemically modified lymphokines according to the invention can be produced, for example, by reacting a lymphokine with the aldehyde of the formula $R-(O-CH_2CH_2)_{n-1}O-CH_2CHO$ (II) wherein R and n are as defined above, in the presence of a reducing agent.

As the boron-containing reducing agent to be used as conducting the reaction, there may be mentioned sodium borohydride and sodium cyanoborohydride. Among them, more preferred is sodium cyanoborohydride from the viewpoint of selectivity of reaction or possibility of carrying out the reaction in the neighborhood of neutrality.

In carrying out the reaction, the aldehyde (II) is used in an amount of about 1 to 10,000 moles per mole of the lymphokine, and the boron-containing reducing agent is used in an amount of about 1 to 100 moles per mole of the lymphokine. The degree of modification can be selected as desired by varying the mole ratio between lymphokine and aldehyde (II). The solvent to be used in carrying out the invention may be any solvent which does not disturb the reaction and is, for example, a buffer such as a phosphate or borate buffer. An organic solvent which does not inactivate lymphokines or disturb the reaction, such as a lower alkanol (e.g. methanol, ethanol, i-propanol) or acetonitrile, may be added. The reaction may be conducted within a broad pH range of 3 to 14 but is preferably perfomred at about pH 7 (pH 6.5–7.5). The reaction temperature may be selected within a broad range of 0° to 80° C., preferably 0° to 50° C., so as not to cause denaturation of lymphokines. A period of 0.5 to 100 hours, generally 10 to 80 hours, will be sufficient for the reaction. The desired, chemically modified lymphokines can be obtained by purifying the reaction mixture by dialysis, salting out, ion exchange chromatography, gel filtration, high performance liquid chromatography, electrophoresis, or the like ordinary method of purifying proteins. The degree of modification of the amino group or groups can be calculated by acid degradation followed by amino acid analysis, for instance.

The above-mentioned aldehyde (II) can be produced from an ethylene glycol derivative of the formula $R-(O-CH_2CH_2)_nOH$ (III) wherein R and n are as defined above, for instance. The following method of producing the same is advantageous in that the production of the corresponding byproduct carboxylic acid is little.

Thus, the compound (III) is oxidized with pyridinium chlorochromate in a haloalkane solvent such as methylene chloride or chloroform. In this case, pyridinium chlorochromate is used in an amount of 1 to 3 moles per mole of compound (III) and the reaction is carried out at −10° to 50° C., preferably at room temperature, for 1 to 30 hours.

Treatment of compound (III) (n-1) with potassium butoxide in t-butanol followed by reaction with a bromoacetal and treatment with an acid such as an organic acid (e.g. trifluoroacetic acid) or an inorganic acid (e.g. hydrochloric or sulfuric acid) can also give the corresponding aldehyde (II) which is longer in chain length by $—O—CH_2CH_2—$ than compound (III). In this case, 10 to 30 moles, per mole of compound (III), of potassium t-butoxide is added to the above compound and, after dissolution 3 to 15 moles, per mole of compound (III), of a bromoacetal is added, followed by reaction at 10° to 80° C. for 0.5 to 5 hours. After treatment of the reaction mixture in the conventional manner, the product is dissolved in a dilute aqueous solution of the above-mentioned acid, followed by heating for 5 minutes to 2 hours.

In each case, the reaction mixture can be subjected to purification processes conventional in the field of chemistry, such as extraction, concentration, recrystallization, reprecipitation, chromatography and/or distillation.

The chemically modified lymphokines according to the present invention have useful physiological activities similar to those of the corresponding known, unmodified lymphokines and are useful as drugs, among other uses.

The chemically modified lymphokines according to the present invention exhibit delay in clearance in vivo as compared with the corresponding known, unmodified lymphokines and are low in toxicity and antigenicity and can be used safely for the same purposes and in the same manner as in the case of known lymphokines.

The chemically modified lymphokines according to the invention can usually by administered to mammals (monkey, dog, pig, rabbit, mouse, human) either orally or parenterally in the form of appropriate pharmaceutical compositions prepared by using carriers, diluents, etc., which are known in themselves.

Thus, for instance, chemically modified IFN-α according to the invention, when used as an antiviral agent, is recommendably administered to human adults once a day by intravenous injection in a dose of $1\times10^4$ to $1\times10^9$ international units.

In the present specification, the amino acids, when referred to by abbreviations, are abbreviated according to IUPAC-IUB (Commision of Biological Nomenclature).

The transformant *Escherichia coli* 294/pHITtrp1101-d2 as disclosed hereinafter in a reference example has been deposited with Institute for Fermentation, Osaka (IFO) under the deposit number IFO-14350 and, since Jun. 6, 1984, with the Fermentation Research Institute (FRI), Agency of Industrial Science and Technology, Ministry of International Trade and Industry under the deposit number FERM BP-703 under Budapest Treaty.

The strain *Escherichia coli* DH1/pTF4 has been deposited with the Institute for Fermentation, Osaka under the deposit number IFO-14299 and, since Apr. 6, 1984, with the FRI under the deposit number FERM BP-628 under Budapest Treaty.

EXAMPLES

Figure 1:
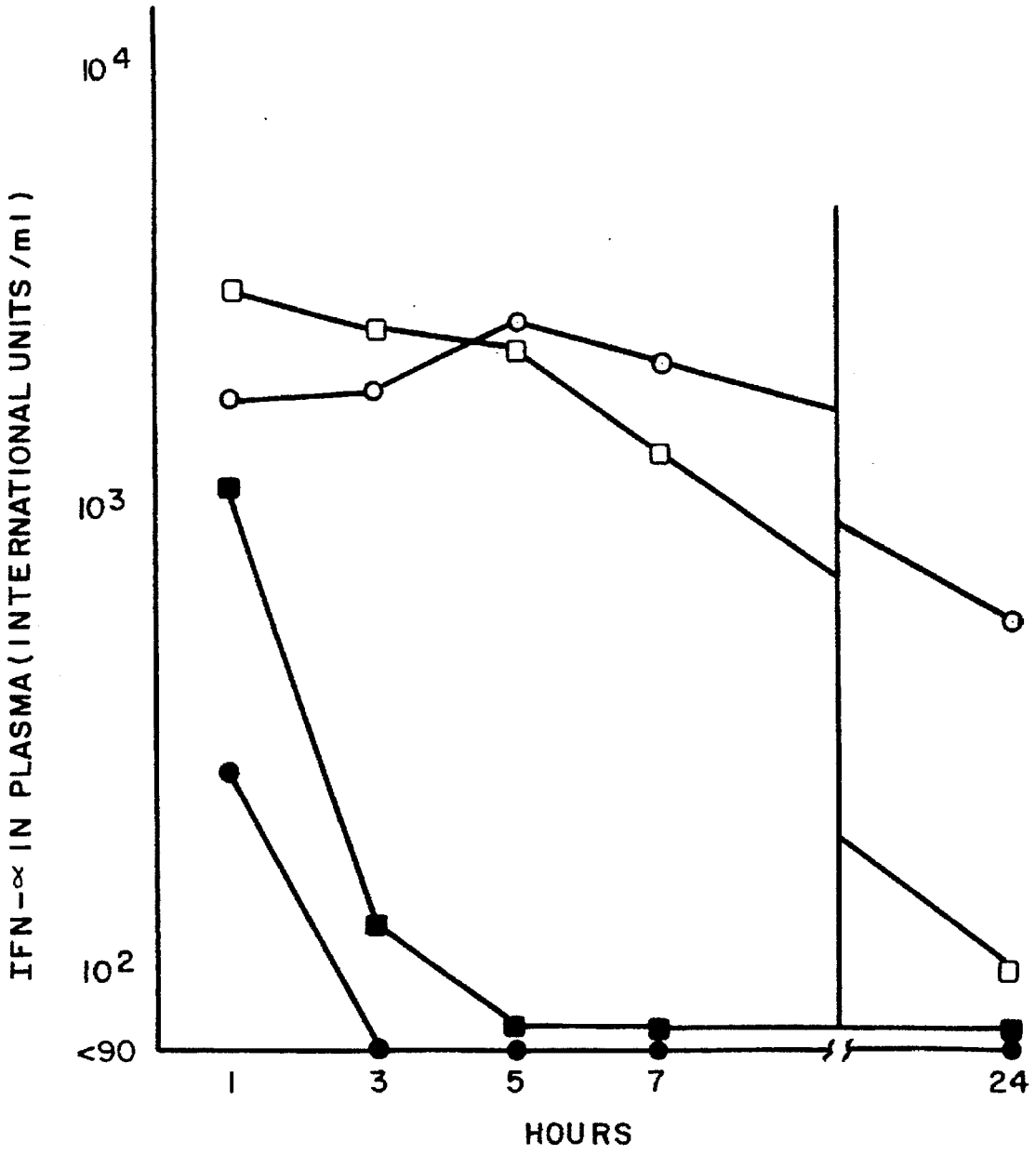
FIG. 1 shows the clearance-delaying effect in rat plasma as disclosed in Example 1 (iv). The measurement results obtained with the chemically modified IFN-α according to the invention as produced in Example 1 (i) are indicated by O (enzyme immunoassay) and □ (antiviral activity assay), and the results obtained with rIFN-αA used as a control by ● (enzyme immunoassay) and ■ (antiviral activity assay.

The following working examples and reference examples illustrate the invention in more detail but are by no means limitative of the invention.

EXAMPLE 1

Production of Polyethylene Glycol Methyl Ether-Modified IFN-α

(i) A 5-ml (4.8 mg as protein) portion of a solution of IFN-α (rIFN-αA) was dialyzed against 0.2M phosphate buffer (pH 7.0) and 0.15M sodium chloride at 4° C. for 12 hours. To the dialyzate taken out, there was added the polyethylene-glycol methyl ether aldehyde (average molecular weight 1,900) (260 mg) obtained in Reference Example 1. Then, sodium cyanoborohydride (140 mg) was added, and the mixture was stirred at 37° C. for 40 hours. The reaction mixture was poured into a Sephadex G-75 column (3.0×43.0 cm) and developed with 25 mM ammonium acetate buffer (pH 5.0) and 0.15M sodium chloride. The eluate was collected in 5-ml portions. Eluate fractions (100–150 ml) containing the contemplated product were combined. Assaying by the Lowry method using bovine serum albumin as a standard revealed that the protein content in the combined fractions was 84 μg/ml. Amino acid ratios in acid hydrolysate (6N hydrochloric acid, 110° C., 24 hours) were as follows: Asp, 12.2 (12); Thr, 10.4 (10); Ser, 16.0 (14); Glu, 24.8 (26); Pro, 6.0 (5); Gly, 6.3 (5); Ala, 8.6 (8); Val, 6.5 (7); Met, 4.0 (5); Ile, 7.6 (8); Leu, 21.0 (21); Tyr, 5.2 (5); Phe, 9.9 (10); Lys, 6.5; His, 3.8 (3); Arg, 9.1 (9); Cys, Trp, decomposed. In view of the fact that rIFN-αA contains 11 Lys residues, the above results led to a conclusion that about 41% of Lys residue in interferon α had been modified as the ε-amino group with the polyethylene glycol methyl ether (average molecular weight 1,900). The potency of this product as determined by the enzyme immunoassay method [Methods in Enzymology, 79, 589–595 (1981)] was $1.51\times10^7$ international units/mg and the antiviral activity as determined by the method described in Journal of Virology, 37, 755–758 (1981) was $0.57\times10^7$ international units/mg. This product (IFA-3) was submitted to a clearance test in rats as mentioned later herein.

(ii) Using 100 mg of the polyethylene glycol methyl ether aldehyde obtained in Reference Example 1 and having an average molecular weight of 750 and 100 mg of sodium cyanoborohydride, rIFN-αA was treated in the same manner as (i) to give 30 ml of a solution of polyethylene glycol methyl ether-modified IFN-α with a protein content of 130 μg/ml. Amino acid ratios in acid hydrolysate (6N hydrochloric acid, 110° C., 24 hours) were as follows: Asp, 12.1 (12); Thr, 10.1 (10); Ser, 13.6 (14); Glu, 26.7 (26); Pro, 5.5 (5); Gly, 5.6 (5); Ala 8.4 (8); Val, 6.7 (7); Met, 5.5 (5); Ile, 7.4 (8); Leu, 21.0 (21); Tyr, 5.1 (5); Phe, 9.6 (10); Lys, 4.7; His, 3.5 (3); Arg, 9.1 (9); Trp, 1.8 (2); Cys, decomposed. The above data indicate that about 57% of Lys residues had been modified at the ε-amino group. Enzyme immunoassay performed in the same manner as (i) gave the result $5\times10^6$ international units/mg, and the antiviral activity of the product was $0.14\times10^8$ international units/mg.

(iii) The produced of (i) was followed using 27 mg of the polyethylene glycol methyl ether aldehyde and 27 mg of sodium cyanoborohydride and there was obtained 50 ml of a polyethylene glycol methyl ether-modified IFN-α solution with a protein content of 45 μg/ml. Amino acid ratios in acid hydrolysate (6N hydrochloric acid, 110° C., 24 hours) gave the following results: Asp, 13.6 (12); Thr, 10.4 (10); Ser, 14.9 (14); Glu, 26.6 (26); Pro, 5.5 (5); Gly, 6.1 (5); Ala, 8.3 (8); Val, 6.6 (7); Met, 5.2 (5); Ile, 7.4 (8); Leu, 21.0 (21); Tyr, 5.3 (5); Phe, 10.2 (10); Lys, 9.0; His, 3.6 (3); Arg, 9.1 (9); Trp, 2.3 (2); Cys, decomposed. The above data indicate that about 18% of Lys residues had been modified at the ε-amino group. Enzyme immunoassay performed in the same manner as (i) gave the result $1.09\times10^8$ international units/mg and the antiviral activity of this product was $1.53\times10^8$ international units/mg.

(iv) The chemically modified IFN-α (IFA-3) of the invention as obtained above in (i) was administered to a group of three 7-week-old female SD rats by injection into the femoral muscle in a dose of $1.274\times10^6$ units per capita. After a prescribed period, blood was sampled from the caudal vein and the IFN-α potency in plasma was determined by the enzyme immunoassay method and antiviral activity method described in Example 1 (i). A distinct delay in clearance was observed as compared with a group administered unmodified interferon α (rIFN-αA) in a dose of $1.259\times10^6$ units per capita.

The above results are depicted in FIG. 1.

EXAMPLE 2

To 5 ml of the solution of chemically modified IFN-α (IFA-3) of the invention as obtained in Example 1 (i), there is added 250 mg of human serum albumin. The resulting solution is filtered through a membrane filter (pore size: 0.2 μm) and distributed into 5 vials, followed by lyophilization and storage. The contents of each vial are dissolved in 1 ml of distilled water for injection just prior to use.

EXAMPLE 3

Production of Polyethylene Glycol Methyl Ether-Modified IFN-α and Alkanoyl-Polyethylene Glycol-Modified IFN-α

(i) The title compounds referred to above were synthesized by using the polyethylene glycol methyl ether aldehyde and alkanoyl-polyethylene glycol aldehyde obtained in Reference Example 1 and Reference Example 2, respectively, and following the procedure of Example 1. Various data for each derivative synthesized are shown in Table 1 and amino acid analysis data therefor in Table 2.

Figure 2:
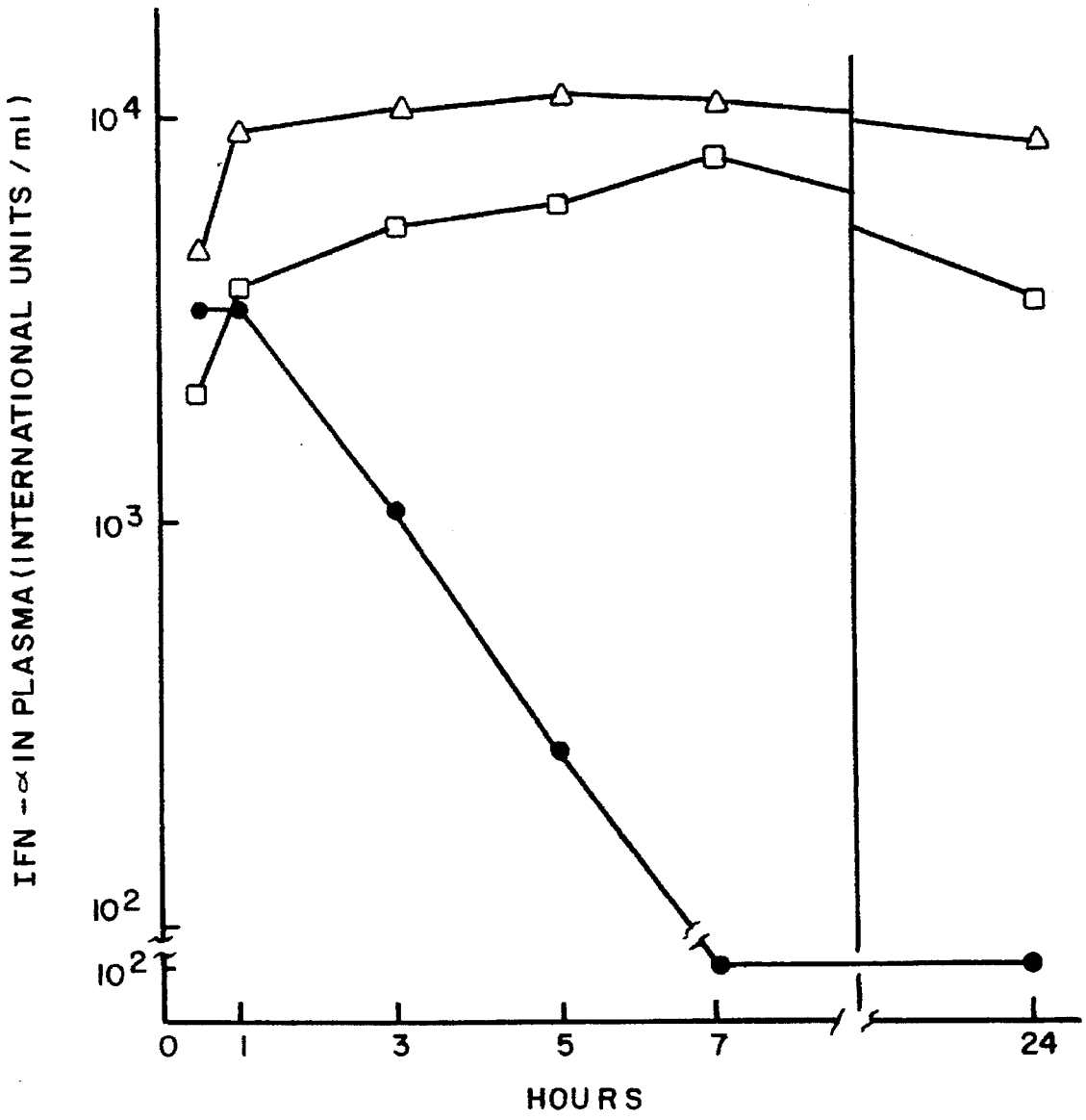
FIG. 2 shows the clearance-delaying effect in rat plasma as disclosed in Example 3 (ii). The data indicated by Δ, □ and ● are the enzyme immunoassay data for compound No. 8, compound No. 2 (Table 1) and control rIFN-αA, respectively.

(ii) The chemically modified IFN-α species obtained in (i) above (compounds No. 2 and No. 8) in Table 1 were administered to 7-week-old female SD rats in groups of 3 by intramuscular injection into the femur in doses of $3.12\times10^6$ units and $2.66\times10^6$ units, respectively. Thereafter, blood samples were collected from the caudal vein at times intervals and assayed for IFN-α potency in plasma by enzyme immunoassay. Obviously delayed clearance was noted as compared with the group given $3.82\times10^6$ units of unmodified IFN-α. These results are depicted in FIG. 2.

TABLE 1

Polyethylene glycol methyl ether-modified interferon α and alkanoyl polyethylene glycol-modified interferon α

| Compound No. | IFN-α amount | PEG aldehyde (Av. mol. wt.) | Reaction temp. °C. | PEG aldehyde amount (mg) |
|---|---|---|---|---|
| 1 | 5 ml (4.2 mg) | MeOPEG (5000) | 37 | 252 (ca. 20 times) |

TABLE 1-continued

| Polyethylene glycol methyl ether-modified interferon α and alkanoyl polyethylene glycol-modified interferon α | | | | |
|---|---|---|---|---|
| 2 | 5 ml (4.2 mg) | MeOPEG (5000) | 37 | 124 (ca. 10 times) |
| 3 | 5 ml (4.2 mg) | MeOPEG (5000) | 37 | 61 (ca. 5 times) |
| 4 | 5 ml (4.2 mg) | MeOPEG (1900) | 37 | 47 (ca. 10 times) |
| 5 | 5 ml (4.2 mg) | MeOPEG (750) | 4 | 110 (ca. 60 times) |
| 6 | 5 ml (4.2 mg) | MeOPEG (550) | 4 | 96 (ca. 70 times) |
| 7 | 5 ml (4.2 mg) | MeOPEG (350) | 4 | 102 (ca. 120 times) |
| 8 | 5 ml (4.2 mg) | Acetyl PEG (1540) | 4 | 184 (ca. 50 times) |
| 9 | 5 ml (4.2 mg) | Caproyl PEG (1100) | 4 | 120 (ca. 50 times) |

| Compound No. | Addition of $NaBH_3CN$ | $NaBH_3CN$ amount (mg) | Reaction time (hours) | Content OD 280 nm |
|---|---|---|---|---|
| 1 | Same time | 50 (ca. 200 times) | 18 | 0.139 |
| 2 | Same time | 54 (ca. 200 times) | 18 | 0.151 |
| 3 | Same time | 52 (ca. 200 times) | 18 | 0.210 |
| 4 | 3 hrs later | 50 (ca. 200 times) | 18 | 0.175 |
| 5 | 5 hrs later | 50 (ca. 200 times) | 24 | 0.100 |
| 6 | 24 hrs later | 100 (ca. 400 times) | 48 | 0.117 |
| 7 | 5 hrs later | 100 (ca. 400 times) | 78 | 0.107 |
| 8 | 7.5 hrs later | 60 (ca. 240 times) | 24 | 0.150 |
| 9 | 9 hrs later | 50 (ca. 200 times) | 24 | 0.087 |

| Compound No. | Obtaines (ml) | Yield (%) | % Modification | EIA AVA |
|---|---|---|---|---|
| 1 | 30 | 99 | 31 | $2.02 \times 10^7$<br>$8.63 \times 10^6$ |
| 2 | 22 | 79 | 18 | $1.30 \times 10^7$<br>$5.53 \times 10^6$ |
| 3 | 20 | 100 | 3.6 | $5.00 \times 10^6$<br>$1.58 \times 10^6$ |
| 4 | 17.5 | 73 | 13 | $3.31 \times 10^6$<br>— |
| 5 | 36 | 84 | 51 | $2.60 \times 10^7$<br>— |
| 6 | 25 | 70 | 46 | $4.70 \times 10^7$<br>— |
| 7 | 36 | 91 | 79 | $1.28 \times 10^7$<br>$2.95 \times 10^7$ |
| 8 | 25 | 89 | 40 | $1.77 \times 10^7$<br>$4.27 \times 10^6$ |
| 9 | 35 | 73 | 56 | $2.57 \times 10^7$<br>— |

PEG: Polyethylene glycol, MeOPEG: Polyethylene glycol methyl ether, The value in parentheses is the average molecular weight.
$NaBH_3CN$: Sodium cyanoborohydride, EIA: Enzyme immounoassay, AVA: Antiviral activity

TABLE 2

| Amino acid analysis value | | | | | | |
|---|---|---|---|---|---|---|
| Compound No. | 1 | 2 | 3 | 4 | 5 | 6 |
| Asp | 12.8 | 12.7 | 12.5 | 12.5 | 13.4 | 12.9 |
| Thr | 11.7 | 11.6 | 11.2 | 10.9 | 11.3 | 11.4 |
| Ser | 15.8 | 16.7 | 15.7 | 15.4 | 17.6 | 15.6 |
| Glu | 27.4 | 27.0 | 26.7 | 27.3 | 27.8 | 27.3 |
| Pro | — | 5.3 | 5.6 | 5.5 | 5.6 | 5.8 |
| Gly | 4.9 | 5.0 | 4.6 | 4.6 | 7.1 | 4.6 |
| Ala | 8.1 | 8.0 | 8.1 | 7.8 | 8.6 | 7.5 |
| Cys | — | — | — | — | — | — |
| Val | 6.8 | 6.8 | 6.7 | 6.6 | 7.3 | 6.7 |
| Met | 3.2 | 4.7 | 4.3 | 4.3 | 4.4 | 4.3 |
| Ile | 7.7 | 7.7 | 7.7 | 7.6 | 8.0 | 7.6 |
| Leu | 21.0 | 21.0 | 21.0 | 21.0 | 21.0 | 21.0 |
| Tyr | 4.3 | 4.5 | 4.6 | 4.6 | 4.9 | 4.6 |
| Phe | 9.8 | 9.8 | 9.8 | 9.8 | 9.8 | 9.8 |
| Lys | 8.6 | 10.3 | 10.6 | 9.6 | 5.4 | 6.1 |
| His | 2.7 | 3.0 | 2.7 | 2.7 | 2.9 | 2.8 |
| Arg | 8.8 | 8.8 | 9.2 | 8.8 | 9.1 | 8.8 |
| Trp | — | — | — | — | — | — |

| Compound No. | 7 | 8 | 9 | rIFN -α A | Theoretical value |
|---|---|---|---|---|---|
| Asp | 12.2 | 12.5 | 12.8 | 12.6 | 12 |
| Thr | 10.9 | 11.6 | 11.3 | 11.6 | 10 |
| Ser | 15.4 | 16.8 | 15.6 | 15.6 | 14 |
| Glu | 26.1 | 26.3 | 26.4 | 27.6 | 26 |
| Pro | 5.5 | 5.7 | 5.7 | 3.7 | 5 |
| Gly | 4.5 | 5.3 | 5.4 | 4.6 | 5 |
| Ala | 7.3 | 8.3 | 8.4 | 7.8 | 8 |
| Cys | — | — | — | — | 4 |
| Val | 6.3 | 6.9 | 7.1 | 6.6 | 7 |
| Met | 4.1 | 4.7 | 4.8 | 3.9 | 5 |
| Ile | 7.3 | 7.5 | 7.6 | 7.6 | 8 |
| Leu | 21.0 | 21.0 | 21.0 | 21.0 | 21 |
| Tyr | 4.4 | 4.8 | 4.8 | 4.6 | 5 |
| Phe | 9.4 | 9.7 | 9.8 | 9.8 | 10 |
| Lys | 2.3 | 6.6 | 4.9 | 11.3 | 11 |
| His | 2.6 | 2.9 | 2.9 | 4.1 | 3 |
| Arg | 8.5 | 7.7 | 7.6 | 8.9 | 9 |
| Trp | — | 0.8 | 1.0 | — | 2 |

—: Not detected.

EXAMPLE 4

Production of Polyethylene Glycol Methyl Ether-Modified Interferon-γ

(i) A 5-ml portion (5.95 mg as protein) of a solution of the interferon-γ protein produced by the recombinant DNA technique (hereinafter abbreviated as rIFN-γ; cf. EPC laid open No. 110044) was applied to a Sephadex G-25 column (2.0×60.0 cm) and developed with 0.2M phosphate buffer (pH 7.0). The eluate wad fractionated in 5-ml portions. Fractions Nos. 11–13 were combined and diluted to 100 ml with the same buffer. Thereto was added polyethylene glycol methyl ether aldehyde (average molecular weight 750) (225 mg), followed by addition of sodium cyanoborohydride (300 mg). The mixture was shaken at 37° C. for 72 hours. The resulting precipitate was removed by centrifugation. The supernatant was concentrated to 10 ml using a Diaflow membrane (Amicon). The concentrate was applied to a Sephadex G-75 column (3.0×43.0 cm) and developed with 25 mM ammonium acetate buffer (pH 6.0)+0.15M sodium chloride+10 mM glutathione. The eluate was fractionated in 5-ml portions. Fractions Nos. 17–24 containing the desired product were combined. The protein content in the combined fractions as determined by the Bradford method using bovine serum albumin as a standard was 7.73 μg/ml. The acid hydrolysate (6N hydrochloric acid, 110° C., 24 hours) gave the following amino acid analysis values: Asp, 19.6 (20); Thr, 4.7 (5); Ser, 8.3 (11), Glu, 18.5 (18); Pro, 2.1 (2); Gly, 5.4 (5); Ala, 7.5 (8); Val, 8.4 (8); Met, 3.7 (4); Ile, 7.1 (7); Leu, 9.7 (10), Tyr, 5.3 (5); Phe, 9.7 (10); Lys, 17.6; His, 2.0 (2); Arg, 5.0 (8); Cys, Trp, decomposed. Since rIFN-γ contains 20 Lys residues, the above results indicate that about 12% of the Lys ε-amino groups in rIFN-γ had been modified by polyethylene glycol methyl ether (average molecular weight 750). The product had an antiviral activity of $1.3\times10^6$ international units/mg. Administration of the product to rats resulted in obvious delay in clearance in blood. On the other hand, the precipitate was dissolved in 6M guanidine hydrochloride and dialyzed against 25 mM ammonium acetate (pH 6.0)+0.15M sodium chloride+10 mM glutathione at 4° C. overnight, followed by Sephadex G-75 gel filtration in the same manner as above. The thus-purified fraction (25 ml) had a protein content of 126 μg/ml and amino acid analysis of the acid hydrolysate (6N hydrochloric acid, 110° C., 24 hours) gave the following values: Asp, 20.0 (20); Thr, 5.2 (5); Ser, 9.5 (11); Glu, 27.8 (18); Pro, 2.7 (2); Gly, 14.6 (5); Ala, 8.1 (8); Val, 8.5 (8); Met, 4.3 (4); Ile, 7.2 (7); Leu, 10.2 (10); Tyr, 5.8 (5); Phe, 10.1 (10); Lys, 14.7; His, 2.0 (2); Arg, 7.3 (8); Thr, 0.7 (1); Cys, decomposed. The higher values for Glu and Gly than the theoretical are presumably due to contamination by glutathione. Since rIFN-γ contains 20 Lys ε-amino groups, the above results indicate that about 26.5% of the Lys ε-amino groups in rIFN-γ had been modified by polyethylene glycol methyl ether.

(ii) Using 225 mg of polyethylene glycol methyl ether aldehyde having an average molecular weight of 750 and 120 mg of sodium cyanoborohydride, rIFN-γ was treated in the same manner as (i) in the presence of 2-mercaptoethanol (2%) to give 30 ml of a polyethylene glycol methyl ether-modified rIFN-γ solution having a protein content of 236 μg/ml. Amino acid analysis of the acid hydrolysate (6N hydrochloric acid, 110° C., 24 hours) gave the following values: Asp, 20.0 (20); Thr, 5.2 (5); Ser, 9.6 (11); Glu, 33.6 (18); Pro, 1.8 (2); Gly, 19.9 (5); Ala, 8.2 (8); Val, 8.9 (8); Met, 4.6 (4); Ile, 7.4 (7); Leu, 10.2 (10); Tyr, 5.9 (5); Phe, 10.7 (10); Lys, 10.2; His, 2.3 (2); Arg, 7.9 (8); Trp, 0.6 (1); Cys, decomposed. The higher values for Glu and Gly are presumably due to contamination with glutathione. Since rIFN-γ contains 20 Lys ε-amino groups, the above results indicate that about 50% of the Lys ε-amino groups in rIFN-γ had been modified by polyethylene glycol methyl ether.

EXAMPLE 5

Production of Polyethylene Glycol Methyl Ether-Modified IFN-γd2

(i) A 5-ml portion (4.95 mg as protein) of the IFN-γd2 solution obtained in Reference Example 3 is applied to a Sephadex G-25 column (2.0×60.0 cm) and developed with 0.2M phosphate buffer (pH 7.0). The eluate is fractionated by 5 ml. Fractions Nos. 11–13 are combined and diluted to 100 ml with the same buffer. To the dilution is added polyethylene glycol methyl ether aldehyde (average molecular weight 750) (200 mg), and then sodium cyanoborohydride (300 mg). The mixtuure is shaken at 37° C. for 72 hours. The resulting precipitate is removed by centrifugation. The supernatant is concentrated to 10 ml using a Diaflow membrane (Amicon). The concentrate is applied to a Sephadex G-75 column (3.0×43.0 cm) and developed with 25 mM ammonium acetate buffer (pH 6.0)+0.15M sodium chloride+10 mM glutathione. The eluate is fractionated by 5 ml, and the fractions containing modified IFN-γd2 having the polyethylene glycol methyl ether moiety on the Lys ε-amino group in the molecule are collected and combined. When this product is administered to rats, evident delay in clearance in blood is noted.

On the other hand, the precipitate is dissolved in 6M guanidine hydrochloride, dialyzed against 25 mM ammonium acetate buffer (pH 6.0)+0.15M sodium chloride+10 mM glutathione at 4° C. overnight, and purified by Sephadex G-75 gel filtration in the same manner as above. Thus is obtained a fraction containing modified IFN-γd2 having the polyethylene glycol methyl ether moiety on the Lys ε-amino group in the molecule.

EXAMPLE 6

Production of Polyethylene Glycol Methyl Ether-Modified IFN-γd3

(i) A 5-ml (5.5 mg as protein) portion of the IFN-γd3 solution obtained in Reference Example 4 is applied to a Sephadex G-25 column (2.0×60.0 cm), followed by development with 0.2M phosphate buffer (pH 7.0). The eluate is fractionated in 5-ml portions. Fractions Nos. 11–13 are combined, and thereto are added polyethylene glycol methyl-ether aldehyde (average molecular weight 750) (225 mg) and then sodium cyanoborohydride (120 mg). The mixture is shaken at 37° C. for 24 hours. The reaction mixture is applied to a Sephadex G-75 column (3.0×43.0 cm), followed by development with 25 mM ammonium acetate buffer (pH 6.0). Thus is obtained a fraction containing modified IFN-γd3 with the polyethylene glycol methyl ether moiety on the Lys ε-amino group in the molecule. When this product is administered to rats, obvious delay in clearance in blood is observed.

EXAMPLE 7

Production of Polyethylene Glycol Methyl Ether-Modified IL-2

(i) A 5-ml (5.0 mg as protein) portion of the interleukin 2 (hereinafter abbreviated as rIL-2) obtained in Reference Example 5 was dialyzed against 0.2M phosphate buffer (pH 7.15) for 12 hours. To the dialyzate was added polyethylene glycol methyl ether aldehyde (average molecular weight 750) (97 mg), and then sodium cyanoborohydride (100 mg). The mixture was stirred at 37° C. for 24 hours. The resultant precipitate was removed by centrifugation. The supernatant was dialyzed against 5 mM ammonium acetate buffer (pH 5.0) for 5 hours. The dialyzate was applied to a Sephadex G-75 column (3.0×43.0 cm) and developed with the same solvent system. The eluate was fractionated in 5-ml portions. The desired product-containing fractions Nos. 21–29 were combined. The combined fraction had a protein content of 25 μg/ml as determined by the Bradford method using bovine serum albumin as a standard. The acid hydrolysate (6N hydrochloric acid, 110° C., 24 hours) gave the following amino acid analysis values: Asp, 12.0 (12); Thr, 12.5 (13); Ser, 7.1 (8); Gly, 18.6 (18); Pro, 5.5 (5); Gly, 2.2 (2); Ala, 5.0 (5); Val, 3.7 (4); Met, 3.9 (4); Ile, 8.1 (8); Leu, 22.2 (22); Tyr, 3.0 (3); Phe, 6.0 (6); Lys, 7.3; His, 3.0 (3); Arg, 3.9 (4); Cys, Trp, decomposed. Since rIL-2 contains 11 Lys residues, the above results indicate that about 33.6% of the Lys ε-amino groups had been modified by polyethylene glycol methyl ether. The IL-2 activity of the product as determined by the method of Hinuma et al. [Biochemical and Biophysical Research Communications, 109, 363–369 (1982)] which measures the growth of an IL-2-dependent mouse natural killer cell line (NKC3) with the [$^3$H]-thymidine uptake into DNA as an index was 22,998 units/mg. When rIL-2 is supposed to have an activity of 40,000 units/mg, the product is estimated to retain 57.7% of the activity. After administration to a male SD rat (5 weeks old) of this product, obvious delay in clearance in blood was noted.

REFERENCE EXAMPLE 1

Synthesis of Polyethylene Glycol Methyl-Ether Aldehyde (i) Polyethylene glycol methyl ether (5 g; average molecular weight 5,000) was dissolved in methylene chloride (100 ml) and then pyridinium chlorochromate (330 mg) was added. The mixture was stirred at room temperature for 12 hours. The reaction mixture was diluted two-fold with methylene chloride and poured into a Florisil column (6×10 cm), and the column was washed with methylene chloride and then with chloroform, followed by elution with methanol-chloroform (1:9). Fractions positive to 2,4-dinitrophenylhydrazine test were combined, the solvent was distilled off under reduced pressure, and there was obtained a crystalline wax. Yield 1.5 g (30%). Thin layer chromatography: $R_f$=0.08 (chloroform-methanol-acetic acid=9:1:0.5, silica gel). $^{13}$C-NMR spectrometry revealed an absorption due to the aldehyde group in hydrated form ($-\underset{=}{C}H(OH)_2$) at 96.2 ppm.

(ii) Polyethylene glycol methyl ether (10 g; average molecular weight 5,000) was dissolved in tertiary-butanol (100 ml). Thereto was added potassium tertiary-butoxide (4.17 g), followed by addition of bromoacetal (2.56 ml). The mixture was stirred at 40° C. for 2 hours. The tertiary-butanol was then distilled of under reduced pressure, water was added to the residue, and the aqueous mixture was extracted with chloroform (200 ml×2). The extract was washed with water and dried over anhydrous sodium sulfate. The chloroform was then distilled off under reduced pressure, petroleum benzine was added to the residue, and the resultant crystalline residue was collected by filtration and washed with ether. Thus was obtained 9.5 mg (95%) of the corresponding polyethylene glycol methyl ether diethyl acetal. A 5-g portion of the acetal was dissolved in 50 ml of 0.05M trifluoroacetic acid, treated in a boiling water bath for 30 minutes and then lyophilized, giving a polyethylene glycol methyl ether aldehyde longer in chain length by $-O-CH_2CH_2-$ than the product obtained in (i).

(iii) Polyethylene glycol methyl ether (5.7 g; average molecular weight 1,900) was dissolved in methylene chloride (100 ml) and then pyridinium chlorochromate (970 mg) was added. The mixture was stirred at room temperature for 12 hours, then diluted with an equal volume of methylene chloride, and poured into a Florisil column (6.0×10.0 cm). The column was washed with methylene chloride and then with chloroform, followed by elution with 10% methanol/chloroform. Fractions positive to 2,4-dinitrophenylhydrazine test were combined. Removal of the solvent by distillation gave a crystalline wax. Yield 1.8 g (30%). Thin layer chromatography: $R_f$=0.10 (chloroform-methanol-acetic acid=9:1:0.5, silica gel). $^{13}$C-NMR spectrometry indicated the presence of an absorption due to the aldehyde group in hydrated form ($-\underset{=}{C}H(OH)_2$) at 96.2 ppm.

(iv) Polyethylene glycol methyl ether (19.5 g; average molecular weight 1,900) was dissolved in tertiary-butanol (100 ml). Potassium tertiary-butoxide (10.4 g) was added and then bromoacetal (6.4 ml) was added. The mixture was stirred at 40° C. for 2 hours. The tertiary-butanol was then distilled off under reduced pressure. Water was added to the residue, followed by extraction with chloroform (200 ml×2). The extract was washed with water and dried over anhydrous sodium sulfate. The chloroform was distilled off under reduced pressure, petroleum benzine was added to the residue, and the resultant crystalline residue was collected by filtration and washed with ether to give 8.5 g (89.5%) of acetal. A 3-g portion of the acetal was dissolved in 0.05M trifluoroacetic acid, and the solution was treated in a boiling water bath for 30 minutes and then lyophilized to give a polyethylene glycol methyl ether aldehyde longer in chain length by $-O-CH_2CH_2-$ than the product obtained in (iii).

(v) Polyethylene glycol methyl ether species having average molecular weights of 750, 550 and 350 were derived from to the corresponding aldehyde species by following the above procedures.

REFERENCE EXAMPLE 2

Synthesis of Alkanoyl Polyethylene-Glycol Aldehyde (i) In 50 ml of pyridine, there was dissolved 15 g of polyethylene glycol 1540 (Wako Pure Chemical Industries) (average molecular weight 1500). To the solution was added 1.85 ml of acetic anhydride. The mixture was stirred at 40° C. for 2 hours and then at room temperature for 16 hours. Thereafter, the solvent was distilled off under reduced pressure. The residue was dissolved in chloroform, and the solution was washed with water, the chloroform layer was dried over anhydrous sodium sulfate, and the chloroform was distilled off under reduced pressure. The residue was dissolved in a small amount of chloroform, a petroleum benzine-ether (2:1) mixture was added to the solution, and the mixture was allowed to stand to give 14 g (90%) of a crystalline wax. A 1.4-g portion of the wax was dissolved in 50 ml of methylene chloride, followed by addition of 300 mg of pyridinium chlorochromate. The resulting mixture was stirred at room temperature for 18 hours. The reaction mixture was applied to a silica gel C-200 (Wako Pure Chemical Industries) column (3×50 cm), and the column was washed with 5% methanol-chloroform (200 ml) and eluted with 10% methanol-chloroform. Fractions positive to the 2,4-dinitrophenylhydrazine test were combined, and the solvent was distilled off under reduced pressure. A crystalline wax was obtained. Yield 580 mg (41%).

(ii) In 50 ml of methylene chloride, there was dissolved 20 g of polyethylene glycol 1000 (Wako Pure Chemical Ind.) (average molecular weight 1000), followed by addition of 5.15 g of n-caproyl anhydride. The mixture was stirred at 70° C. for 2 hours. Then, the solvent was distilled off, and the residue was purified using a silica gel C-200 column (3×50 cm) and elution with ethyl acetate-methanol (4:1) to give 14.9 g (60%) of an oil, which solidified upon standing in a refrigerator. The subsequent oxidation with pyridinium chlorochromate as conducted in the same manner as (i) gave the corresponding aldehyde.

REFERENCE EXAMPLE 3

Production of IFN-γd2

(i) Transformant preparation

The IFN-γ expression plasmid pHITtrp1101 [cf. EPC (laid open) No. 110044, Example 2 (iii)] was digested with the restriction enzymes AvaII and PstI, and an AvaII-PstI 1 kb DNA fragment containing the IFN-γ gene portion was isolated. The protein synthesis start codon-containing oligonucleotide adapter

CGATAATGTGCCAG
TATTACACGGTCCTG chemically synthesized by the phosphotriester method was joined to the above DNA fragment at the AvaII cohesive end thereof using T4 DNA ligase.

Figure 3:
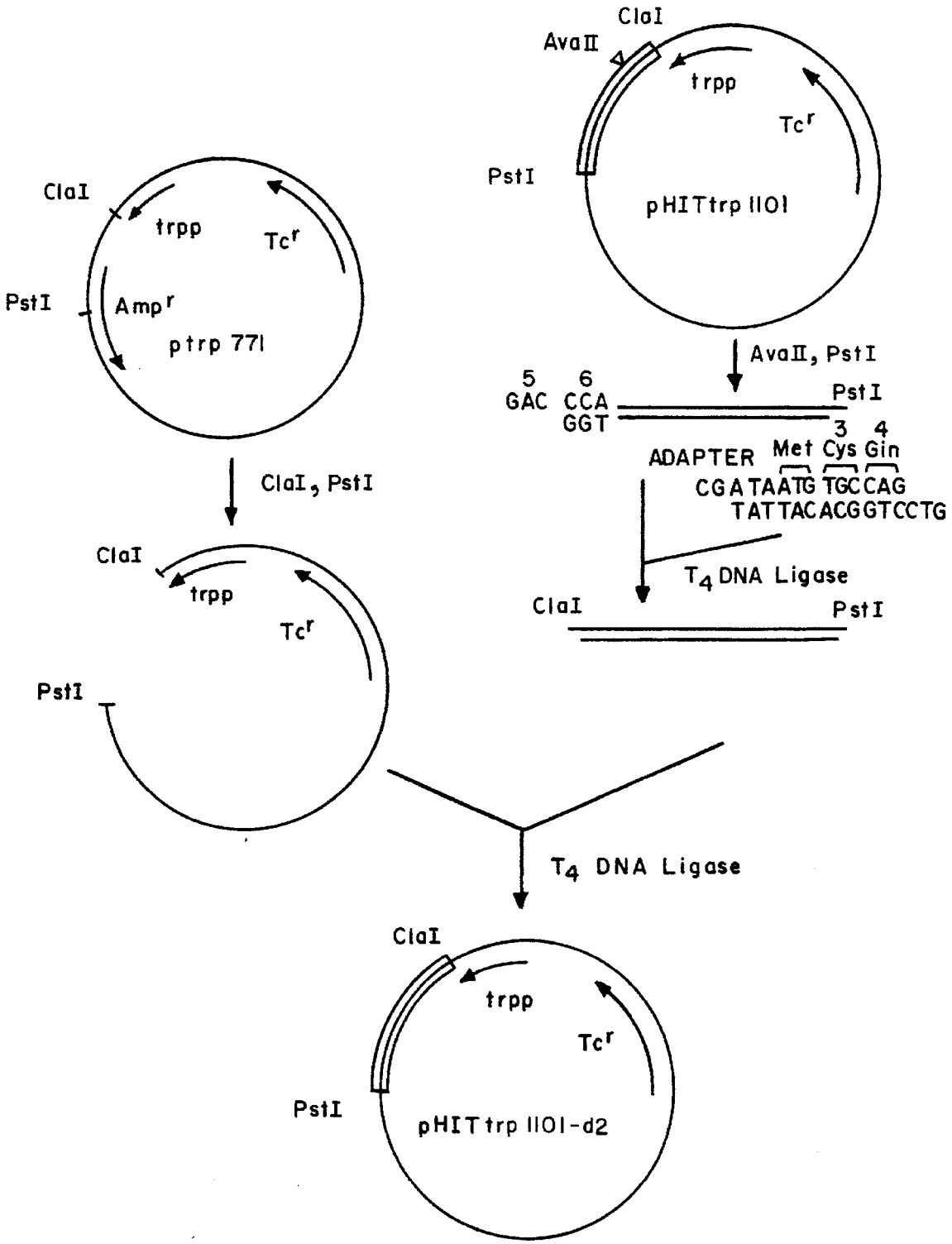
FIG. 3 shows the construction scheme for the expression plasmid pHITtrp1101-d2 disclosed in Reference Example 3 (i) and FIG. 4 the construction scheme for the expression plasmid pLC2 disclosed in Reference Example 4 (i).
Figure 4:
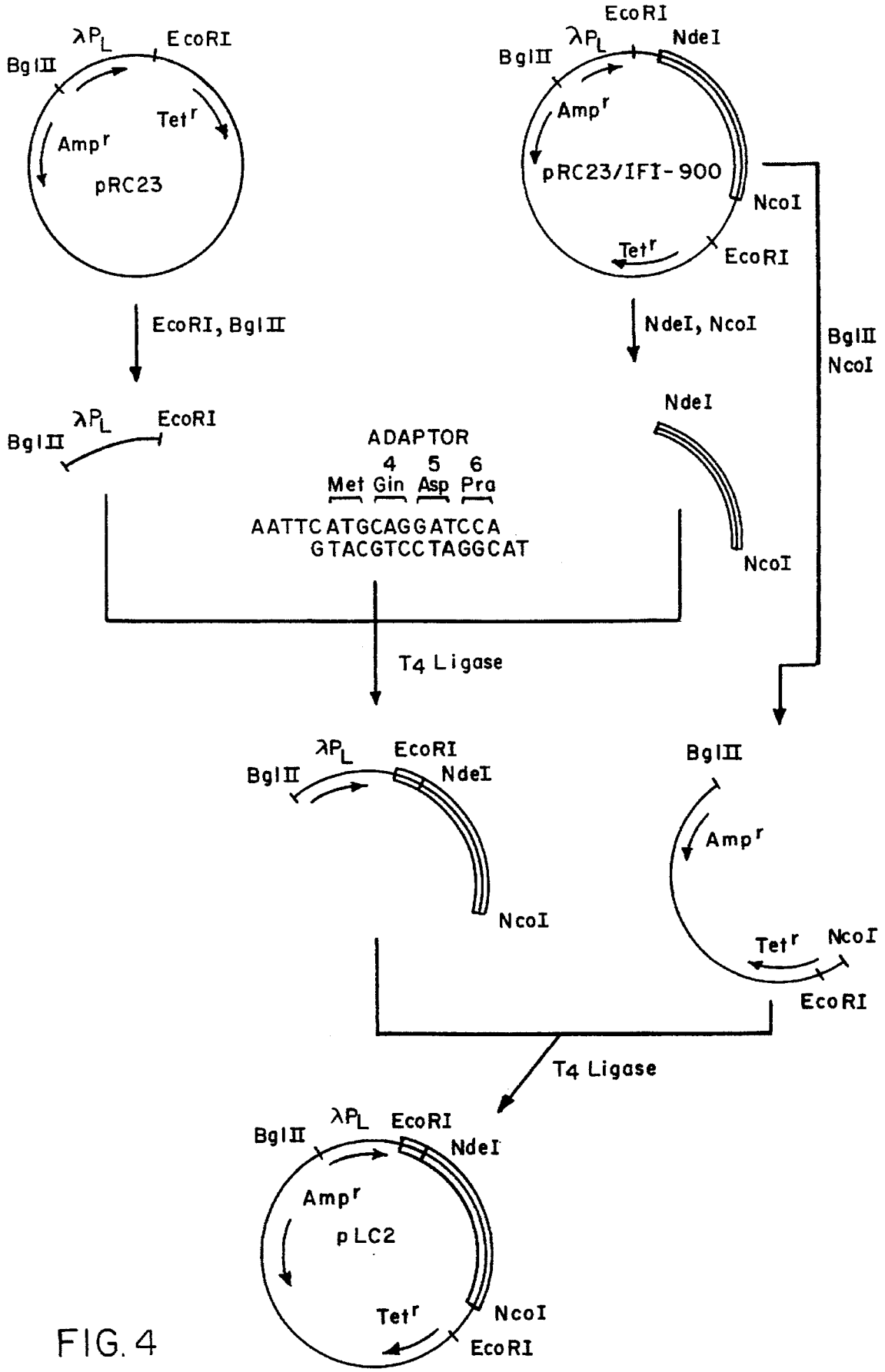

The above adapted-joined gene was inserted into the DNA fragment obtained by cleavage of the plasmid ptrp771 [cf. above-cited publication, Example 2 (ii)] with the restriction enzymes ClaI and PstI, downstream from the trp promoter in said fragment. Thus was constructed the expression plasmid phITtrp1101-d2 coding for the 1 2
Cys—Tyr-deficient IFN-γ polypeptide (FIG. 3).

*Escherichia coli* 294 was transformed with this plasmid pHITtrp1101-d2 by the method of Cohen et al. [Proc. Natl. Acad. Sci. U.S.A., 69, 2110 (1972)] to give the transformant *Escherichia coli* (=*E. coli*) 294/pHITtrp1101-d2 carrying said plasmid.

(ii) Transformant cultivation

The strain *E. coli* 294/pHITtrp 1101-d2 carrying the plasmid constructed in (i) above was cultivated in M9 medium containing 8 μg/ml of tetracycline, 0.4% of casamino acids and 1% of glucose at 37° C. When the growth reached KU 220, 3-β-indolylacrylic acid (IAA) was added to a concentration of 25 μg/ml. Thereafter, the cultivation was continued for further 4 hours. After cultivation, cells were harvested by centrifugation and suspended in 1/10 volume of 0.05M Tris-HCl (pH 7.6) containing 10% sucrose. To the suspension, there were added phenylmethylsulfonyl fluoride, NaCl, ethylenediaminetetraacetate (EDTA), spermidine and lysozyme to concentrations of 1 mM, 10 mM, 40 mM and 200 μg/ml, respectively. After standing at 0° C. for 1 hour, the suspension was treated at 37° C. for 3 minutes to give a lysate.

The lysate was subjected to centrifugation at 4° C. and 20,000 rpm (Servall centrifuge, SS-34 rotor) for 30 minutes to given an IFN-γd2 polypeptide-containing supernatant. This supernatant had an antiviral activity of $2.87\times10^8$ U/liter culture fluid.

(iii) Purification of IFN-γd2

In 18 ml of 0.1M Tris-hydrochloride buffer (pH 7.0) containing 7M guanidine hydrochloride and 2 mM phenylmethylsulfonyl fluoride, there were suspended 5.9 g of cells obtained in the same manner as (ii) above and stored in the frozen state. The suspension was stirred at 4° C. for 1 hour and then subjected to centrifugation at 10,000 x g for 30 minutes to give 20 ml of a supernatant. This supernatant was diluted with 260 ml of a buffer (pH 7.4) comprising 137 mM sodium chloride, 2.7 mM potassium chloride, 8.1 mM disodium phosphate and 1.5 mM monopotassium phosphate (hereinafter such buffer being referred to by the abbreviation PBS) and the dilution was applied to an antibody column (Mcγ2-11.1, column volume 12 ml) at a flow rate of 1 ml/minute. The column was then washed with 60 ml of 20 mM sodium phosphate buffer (pH 7.0) containing 0.5M guanidine hydrochloride and eluted with 36 ml of 20 mM sodium phosphate buffer (pH 7.0) containing 2M guanidine hydrochloride to give 20 ml of an antivirally active fraction.

This 20-ml fraction was applied to a Sephacryl S-200 (Pharmacia) column (2.6×94 cm, column volume 500 ml) equilibrated in advance with 25 mM ammonium acetate buffer (pH 6.0) containing 1 mM ethylenediaminetetraacetate, 0.15M sodium chloride, 10 mM cysteine and 2M guanidine hydrochloride, followed by eltuion with the same buffer. Thus was obtained 37 ml of the antivirally active fraction.

The 1 2
Cys—Tyr-deficient

IFN-γ polypeptide (IFN-γd2) obtained weighed 5.9 mg and had a specific activity of $1.0\times10^7$ U/mg.

REFERENCE EXAMPLE 4

Production of IFN-γ d3

(i) Transformant production

The IFN-γ expression plasmid pRC23/IFI-900 [cf. Example 7 of the specification for a patent application under EPC as laid open under No. 0089676] was digested with the restriction enzymes NdeI and NcoI, and a 710 bp NdeI-NcoI DNA fragment (A) containing the IFN-γ gene region was isolated. Separately, the plasmid pRC23 was digested with the restriction enzymes BglII and EcoRI, and a 265 bp DNA fragment (B) containing the $\gamma P_L$ promoter was isolated. The fragments (A) and (B) and the chemically synthesized, protein synthesis start codon-containing oligonucleotide

AATTCATGCAGGATCCA
GTACGTCCTAGGTAT were joined together using T4 DNA ligase, with the NdeI and EcoRI cohesive ends as the sites of joining. The DNA fragment thus obtained was joined to the plasmid pRC23/IFI-900 after treatment with NcoI and BglII, to thereby construct an expression plasmid, pLC2, coding for the 1 2 3
Cys—Tyr—Cys-deficient IFN-γ polypeptide (FIG. 2). This plasmid pLC2 was used for transforming *Escherichia coli* RRI (pRK248 cIts) by the method of Cohen et al. [supra] to give a transformant, *Escherichia coli* (=*E. coli*) PRI (pLC2,pRK248 cIts).

(ii) Transformant cultivation

The strain *E. coli* RRI (pLC2,pRK248 cIts) carrying the plasmid constructed in (i) above was shake-cultured at 35° C. in 50 ml of a liquid medium containing 1% Bactotryptone, 0.5% yeast extract, 0.5% sodium chloride and 7 μg/ml tetracycline. The culture broth was transferred to 2.5 liters of M9 medium containing 0.5% casamino acid, 0.5% glucose and 7 μg/ml tetracycline, and grown at 35° C. for 4 hours and then at 42° C. for 3 hours. Cells were harvested by centrifugation and stored at −80° C.

(iii) Purification

In 22 ml of 0.1M Tris-hydrochloride buffer (pH 7.0) containing 7M guanidine hydrochloride and 2 mM phenylmethylsulfonyl fluoride, there were suspended 7.1 g of frozen cells obtained in the same manner as mentioned above in (ii). The suspension was stirred at 4° C. for 1 hour and then centrifuged at 10,000 x g for 30 minutes to give 24 ml of a supernatant. This supernatant was diluted by adding 300 ml of PBS and the dilution was applied to an antibody column (Mcγ2-11.1, column capacity 15 ml) at a flow rate of 1 ml/minute. Thereafter, the column was washed with 60 ml of 20 mM sodium phosphate buffer (pH 7.0) containing 0.5M guanidine hydrochloride and then eluted with 45 ml of 20 mM sodium phosphate buffer (pH 7.0) containing 2M guanidine hydrochloride, to give 25 ml of an antivirally active fraction. This fraction (25 ml) was applied to a Sephacryl S-200 (Pharmacia) column (2.6×94 cm; column capacity 500 ml) equilibrated in advance with 25 mM ammonium acetate buffer (pH 6.0) containing 1 mM ethylenediaminetetraacetic acid, 0.15M sodium chloride, 10 mM cysteine and 2M guanidine hydrochloride, and eluted with the same buffer to give 40 ml of an antivirally active fraction.

The thus-obtained 1 2 3
Cys—Tyr—Cys-deficient

IFN-γ polypeptide IFN-γ d3 weighed 7.0 mg and had a specific activity of $2.72\times10^7$ IU/mg.

REFERENCE EXAMPLE 5

Production of Non-Glycosylated Human IL-2

(i) Transformant cultivation

*E. coli* DH1/pTF4 [U.S. pat. appln. Ser. No. 674,556] was inoculated into 50 ml of a liquid medium (pH 7.0) containing 1% Bacto tryptone (Difco Laboratories, USA), 0.5% Bacto yeast extract (Difco Laboratories, USA), 0.5% sodium chloride and 7 μg/ml tetracycline as placed in a 250-ml Erlenmeyer flask. After incubation at 37° C. overnight on a swing rotor, the culture medium was transferred to a 5-liter jar fermenter containing 2.5 liters of M9 medium containing 0.5% casamino acid, 0.5% glucose and 7 μg/ml tetracycline. Incubation was then conducted with aeration and stirring at 37° C. for 4 hours and, after addition of 3-β-indolylacrylic acid (25 μg/ml), for further 4 hours. Cells were harvested from the thus-obtained 2.5-liter culture broth by centrifugation, frozen at −80° C. and stored.

(ii) Extraction

The freeze-stored cells (12.1 g) obtained above were suspended uniformly in 100 ml of an extractant (pH 7.0) containing 7M guanidine hydrochloride and 0.1M Tris.HCl, the suspension was stirred at 4° C. for 1 hour and the lysate was centrifuged at 28,000 x g for 20 minutes. There was obtained 93 ml of a supernatant.

(iii) Purification of IL-2 protein

The supernatant obtained above was dialyzed against 0.01M Tris.HCl buffer (pH 8.5) and then centrifuged at 19,000 x g for 10 minutes, giving 94 ml of a dialyzate supernatnat. This dialyzate supernatant was applied to a DE 52 (DEAE-cellulose, Whatman, Great Britain) column (50 ml in volume) equilibrated with 0.01M Tris-HCl buffer (pH 8.5) for protein adsorption. IL-2 was eluted making a linear NaCl concentration gradient (0–0.15M NaCl, 1 liter). The active fractions (53 ml) were concentrated to 4.8 ml using a YM-5 membrane (Amicon, USA) and subjected to gel filtration using a Sephacryl S-200 (Pharmacia, Sweden) column (500 ml in volume) equibrated with 0.1M Tris.HCl (pH 8.0)-1M NaCl buffer. The active fractions (28 ml) obtained were concentrated to 2.5 ml using a YM-5 membrane. The concentrate was applied to a Ultrapore RPSC (Altex, USA) column for adsorption, and high performance liquid chromatography was performed using a trifluoroacetic acid-acetonitrile system as the eluent.

An active fraction was collected at a retention time of 39 minutes under the following conditions: column, Ultrapore RPSC (4.6×75 mm); column temperature, 30° C.; eluent A, 0.1% trifluoroacetic acid-99.9% water; eluent B, 0.1% trifluoroacetic acid-99.9% acetonitrile; elution program, minute 0 (68% A+32% B)—minute 25 (55% A+45% B)—minute 35 (45% A+55% B)—minute 45 (30% A+70% B)—minute 48 (100% B); elution rate, 0.8 ml/min.; detection wave length, 230 nm. Thus was obtained 10 ml of a solution containing 0.53 mg of non-glycosylated human IL-2 protein [specific activity, 40,000 U/mg; activity recovery from starting material, 30.6%; purity of protein, 99% (determined by densitometry)].

The following references, which are referred to for their disclosures at various points in this application, are incorporated herein by reference.

U.S. Pat. No. 4,002,531
Methods in Enzymology, 47, 469–478 (1977)
Japanese Patent Unexamined Publication No. 154,596/83
U.S. patent application Ser. No. 685,819
U.S. patent application Ser. No. 534,038
E.P. Patent Publication 104798
Method in Enzymology, 79, 589–595 (1981)
Journal of Virology, 37, 755–758 (1981)
E.P. Patent Publication 110044
Proc. Natl. Acad. Sci. USA, 69, 2110 (1972)
E.P. Patent Publication 0089676
U.S. patent application Ser. No. 674,556

What is claimed is:

1. A process of making an activated polyethylene glycol methyl ether aldehyde for the modification of proteins, the process comprising the steps of:

(a) dissolving a polyethylene glycol methyl ether aldehyde in a 0.2M phosphate buffer at pH 7.0; and (b) adding sodium cyanoborohydride to the solution obtained in step (a).

* * * * *